(12) United States Patent
Schade et al.

(10) Patent No.: US 12,228,504 B2
(45) Date of Patent: Feb. 18, 2025

(54) MATERIAL EVALUATING ARRANGEMENT FOR AN AGRICULTURAL WORK MACHINE

(71) Applicant: Deere & Company, Moline, IL (US)

(72) Inventors: Peter Schade, Bad Dürkheim (DE); Helge Klein, Kaiserslautern (DE); Frank Weber, Kaiserslautern (DE)

(73) Assignee: Deere & Company, Moline, IL (US)

( * ) Notice: Subject to any disclaimer, the term of this patent is extended or adjusted under 35 U.S.C. 154(b) by 844 days.

(21) Appl. No.: 17/248,895

(22) Filed: Feb. 12, 2021

(65) Prior Publication Data

US 2021/0247305 A1    Aug. 12, 2021

(30) Foreign Application Priority Data

Feb. 12, 2020  (DE) .......................... 102020000904.2

(51) Int. Cl.
*G01N 21/3577*    (2014.01)
*A01C 23/00*    (2006.01)
(Continued)

(52) U.S. Cl.
CPC ....... *G01N 21/3577* (2013.01); *A01C 23/007* (2013.01); *A01D 41/1277* (2013.01);
(Continued)

(58) Field of Classification Search
CPC .. G01N 21/3577; G01N 21/274; G01N 21/31; G01N 21/3563; G01N 21/359;
(Continued)

(56) References Cited

U.S. PATENT DOCUMENTS 10,254,215 B2    4/2019  Wilk et al.
2002/0039186 A1*  4/2002  Rosenberg ......... G01N 21/8507
                                                       356/432
(Continued)

FOREIGN PATENT DOCUMENTS

DE    102011076677 A1    12/2012
DE      19922867 C5      4/2015
(Continued)

OTHER PUBLICATIONS

Liang, Xiu Ying, et al. "Study of sample temperature compensation in the measurement of soil moisture content." Measurement 44.10 (2011): 2200-2204. (Year: 2011).*
(Continued)

*Primary Examiner* — Dominic J Bologna
(74) *Attorney, Agent, or Firm* — HANLEY, FLIGHT & ZIMMERMAN, LLC

(57) ABSTRACT

A material evaluating device for an agricultural work machine comprising: a light source for illuminating one or more constituent materials to be examined; a spectrometer for providing a spectral signal related to the wavelength-specific intensity of light reflected by the constituent materials; and an evaluation device configured to determine the content of one or more constituent materials using the spectral signal of the spectrometer and a calibration data, wherein a property signal relating to a property of the one or more constituent materials is supplied to the evaluation device and the evaluation device is configured, using the property signal, to determine the content of the one or more constituent materials.

20 Claims, 2 Drawing Sheets

(51) Int. Cl.
  *A01D 41/127*    (2006.01)
  *G01N 21/27*     (2006.01)
  *G01N 21/31*     (2006.01)
  *G01N 21/3563*   (2014.01)
  *G01N 21/359*    (2014.01)
  *G01N 21/84*     (2006.01)
  *G01N 33/02*     (2006.01)
  *G06N 3/045*     (2023.01)
  *G06N 3/08*      (2023.01)

(52) U.S. Cl.
  CPC ........... *G01N 21/274* (2013.01); *G01N 21/31* (2013.01); *G01N 21/3563* (2013.01); *G01N 21/359* (2013.01); *G01N 33/02* (2013.01); *G06N 3/045* (2023.01); *G06N 3/08* (2013.01); *G01N 2021/8466* (2013.01); *G01N 2201/1211* (2013.01); *G01N 2201/1214* (2013.01); *G01N 2201/1218* (2013.01); *G01N 2201/127* (2013.01); *G01N 2201/1296* (2013.01)

(58) Field of Classification Search
  CPC ........... G01N 33/02; G01N 2021/8466; G01N 2201/1211; G01N 2201/1214; G01N 2201/1218; G01N 2201/127; G01N 2201/1296; A01C 23/007; A01D 41/1277; G06N 3/045; G06N 3/08
  See application file for complete search history.

(56) References Cited

U.S. PATENT DOCUMENTS

| | | | |
|---|---|---|---|
| 2004/0021077 A1* | 2/2004 | Ambuel | G01N 21/3563 250/339.02 |
| 2010/0110428 A1* | 5/2010 | Priesnitz | G01J 3/02 56/10.1 |
| 2011/0054864 A1* | 3/2011 | Lundstedt | G01N 35/00871 703/2 |
| 2018/0271015 A1* | 9/2018 | Redden | G06N 3/08 |
| 2022/0390362 A1* | 12/2022 | Liran | G06N 20/00 |
| 2023/0393062 A1* | 12/2023 | Stone | G06N 3/0464 |

FOREIGN PATENT DOCUMENTS

| | | |
|---|---|---|
| DE | 102017220103 A1 | 5/2019 |
| DE | 102018213215 A1 | 2/2020 |
| DE | 102018216498 A1 | 3/2020 |
| EP | 1488214 B1 | 2/2012 |
| EP | 3444577 A1 | 2/2019 |
| NL | 1015440 C2 | 12/2001 |
| WO | WO9821930 A1 | 5/1998 |
| WO | WO2005083386 A1 | 9/2005 |

OTHER PUBLICATIONS

English machine translation of Bohrer et al. (DE 102018213215 A1), (Year: 2018).*

German Search Report issued in counterpart application No. 102020000904.2 dated Oct. 12, 2020 (08 pages).

J. B. Reeves III et al., Near-Infrared Spectroscopic Determination of Carbon, Total Nitrogen, and Ammonium-N in Dairy Manures, Journal of Dairy Science vol. 83, No. 8, dated Mar. 2, 2000, pp. 1829-1836.

C. Paul et al., Influence of sample temperature on the assessment of quality characteristics in undried forages by Near Infrared Spectroscopy (NIRS), Landbauforschung Völkenrode Apr. 2002, pp. 229-237.

A. Peinado et al., Temperature-induced variation for NIR tensor-based calibration, Chemometrics and Intelligent Laboratory Systems 83 (2006), dated Jan. 17, 2006, pp. 75-82.

Groß et al., Multivariate Korrektur des Temperatureinflusses in der NIR-spektroskopischen Materialfeuchtebestimmung, Dissertation, Göttingen, 2009.

J. M. Roger et al., EPO-PLS external parameter orthogonalization of PLS application to temperature-independent measurement of sugar content of intact fruits, Chemometrics and intelligent laboratory system, 2003, vol. 66 (2), pp. 191-204.

Extended European Search Report and Written Opinion issued in European Patent Application No. 21151863.4, dated Jun. 28, 2021, in 11 pages.

Xiu Ying Liang et al., Study of sample temperature compensation in the measurement of soil moisture content, Jul. 6, 2011, pp. 2200-2204.

F. Chauchard et al., Correction of the temperature effect on near infrared calibration-application to soluble solid content prediction, Near Infrared Spectrosc, Jan. 1, 2004, pp. 199-205.

* cited by examiner

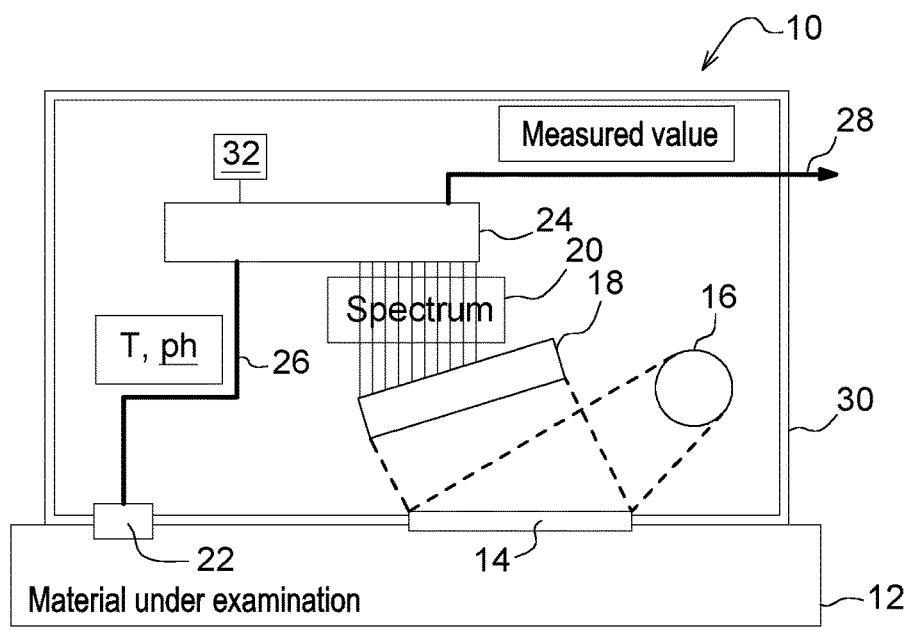
FIG. 1
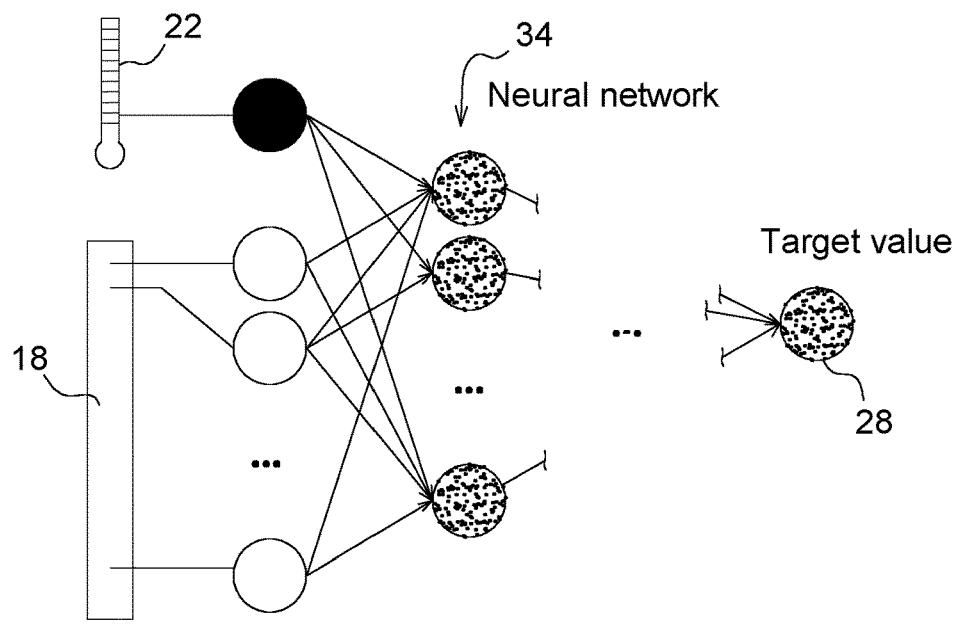
FIG. 2
FIG. 3

MATERIAL EVALUATING ARRANGEMENT FOR AN AGRICULTURAL WORK MACHINE

RELATED APPLICATIONS

This document claims priority based on German Patent Application No. 102020000904.2, filed on Feb. 12, 2020, which is hereby incorporated by reference into this application.

DESCRIPTION

The disclosure relates to a material evaluating arrangement for an agricultural work machine.

BACKGROUND

The measurement of constituent materials on the basis of optical spectroscopy, in particular near-infrared spectroscopy, is used in many applications including, for example, in the foodstuffs industry and in agriculture. With respect to agriculture, optical spectroscopy may be used to investigate the state of crops growing on a field, of constituent materials of harvested crop parts, or the composition of liquid manure.

SUMMARY

A material evaluating device for an agricultural work machine comprising: a light source for illuminating one or more constituent materials to be examined; a spectrometer for providing a spectral signal related to the wavelength-specific intensity of light reflected by the constituent materials; and an evaluation device configured to determine the content of one or more constituent materials using the spectral signal of the spectrometer and a calibration data, wherein a property signal relating to a property of the one or more constituent materials is supplied to the evaluation device and the evaluation device is configured, using the property signal, to determine the content of the one or more constituent materials.

DRAWINGS

The above-mentioned aspects of the present disclosure and the manner of obtaining them will become more apparent and the disclosure itself will be better understood by reference to the following description of the embodiments of the disclosure, taken in conjunction with the accompanying drawing, wherein:

FIG. 1 shows a schematic view of a material evaluating arrangement;

FIG. 2 shows a flow diagram related to obtaining the calibration data and evaluating the spectra;

FIG. 3 shows a scheme for an evaluation of the signals of a spectrometer by means of a self-learning system making use of a neural network;

DETAILED DESCRIPTION

Figure 4:
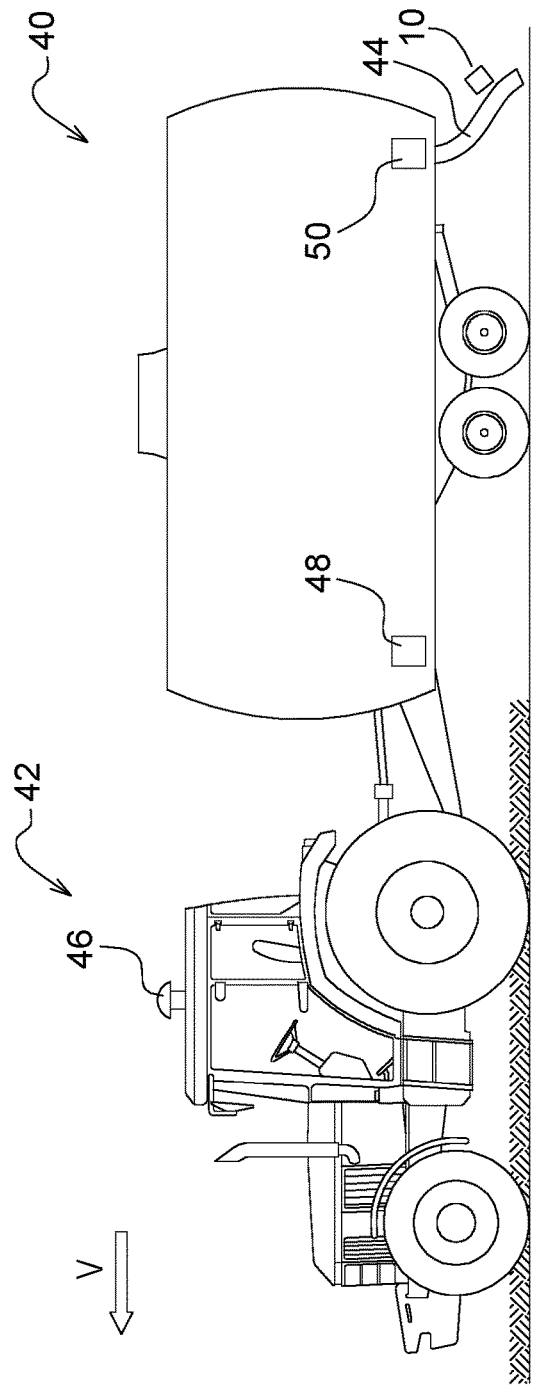
FIG. 4 shows a side view of an agricultural work machine in the form of a manure tank with a spectrometer arrangement.

A material evaluating arrangement suitable for attachment to an agricultural work machine comprises a light source for illuminating a sample to be examined, a spectrometer for providing a spectral signal related to the wavelength-specific intensity of light reflected and/or transmitted by the sample, and an evaluation device that is configured to determine the content of one more constituent materials in the sample on the basis of the spectral signal of the spectrometer and of stored calibration data. A signal or a plurality of signals related to one or more properties of the sample can be supplied to the evaluation device, and the evaluation device is configured to take the signal or signals into consideration in the determination of the content of the one or more constituent materials in the sample.

The signal can be generated by a sensor that interacts with the sample or can be entered into the evaluation device by means of an interface. According to the second variant, an operator can thus measure the property or read it from another measuring device, or at least estimate it and enter it into the evaluation device via the interface.

The signal can relate inter alia to one or more of the following properties of the sample: temperature, pressure, pH value, flow rate and/or air humidity in the surroundings of the sample etc. In the application of spectrometers to agricultural work machines, a measurement of the temperature or of another property of the sample has until now been avoided. Typically, enhanced calibration models have been used for evaluating the spectra, in which the dependency of the measurement on the temperature or other property is already contained in the spectra used, resulting in lower accuracy.

The evaluation device can be operated to modify the spectral signal on the basis of the signal and/or to modify and/or to select the calibration data for the determination of the content of the one or more constituent materials in the sample and/or to determine the content of the one more constituent materials in the sample on the basis of calibration data that are independent of the property and to correct this on the basis of the property. It is also possible to generate the calibration data through a self-learning algorithm (calibration data generation device), e.g. a neural network.

This spectrometer arrangement can, in particular, be used on an agricultural work machine, wherein the content of the one or more constituent materials in the sample measured by the spectrometer arrangement, which can, for example, be crops growing on a field, harvested crops or liquid manure, is stored in a geo-referenced manner for documentation purposes and/or used for the control of an actuator.

The work machine can in particular comprise a manure tank, and the spectrometer arrangement can interact with the content of the manure tank or the liquid manure flowing into or out of it, in order to control the application rate of the liquid manure onto a field on the basis of the content of the one or more constituent materials in the sample acquired by the spectrometer arrangement.

The prediction of the constituent material values is generally understood as:

$$\text{constituent materials} = \sum_i \text{spectrum} * \text{coefficients} + \text{offset}$$

This prediction usually takes place through the application of a linear model in the form of The intensities of the components of the spectrum are thus multiplied by coefficients associated with the value of i and added together. The coefficients and the offset are specified through appropriate linear regression methods (calibration algorithm) based on a learning dataset of spectra together with associated metadata, the constituent material values determined in the laboratory independently of the spectroscopic measurement. A number of samples, each having known proportions of constituent materials, are thus subjected to a spectroscopic measurement in order to determine, for each of the wavelengths examined, the associated coefficients and the offset for a constituent material to be investigated. These calibration data are finally stored, and used in a subsequent measurement of an unknown sample to ascertain the proportion of the constituent material on the basis of the recorded spectrum (see J. B. Reeves III et al., *Near-Infrared Spectroscopic Determination of Carbon, Total Nitrogen, and Ammonium-N in Dairy Manures*, J Dairy Sci 83 (2000), pages 1829-1836).

The temperature and other parameters such as the pressure have an influence on the spectrum measured in the measurement for many constituent materials, for example for liquids such as liquid manure. An approach to the solution of this problem consists in recording samples at different temperatures in the learning dataset (cf. for example C. Paul et al., *Influence of sample temperature on the assessment of quality characteristics in undried forages by Near Infrared Spectroscopy (NIRS)*, Landbauforschung Völkenrode April 2002, pages 229-237, A. Peinado et al., Temperature-induced variation for NIR tensor-based calibration, Chemometrics and Intelligent Laboratory Systems 83 (2006), pages 75-8 or WO 2005/083386 A1). The calibration algorithm here only "ascertains" the changes in the spectra brought about by a change in the constituent materials, since the spectral changes resulting from temperature change do not correlate with a change in the constituent material.

For a linear calibration model, such an approach is the most obvious possibility for making the calibration model robust in respect of temperature influences. The disadvantage of this method is a loss of sensitivity (accuracy), since the spectral changes that are caused by the marginal parameters (temperature, pressure, etc.) can mask the changes that result from the variation in the constituent materials. This is, nevertheless, the procedure usually applied in agriculture, especially since it does not require an acquisition of the temperature of the sample or of other marginal parameters. The effects of the expected variations in the temperature are already contained in the calibration model (enhanced in respect of the temperature variations), even though at the expense of accuracy.

Another procedure consists in carrying out a temperature compensation in the reference value space is using a calibration transfer method. By adapting the predicted values on the basis of the linear regression, the values measured at a temperature other than that used during the referencing can be transformed back to the reference values measured at the reference temperature ("bias and skew adjustment", also known as a posteriori correction). A linear equation is applied here in order to correct the proportions of constituent materials derived from the spectra in a temperature-dependent manner. A further approach provides for shifting the entire spectral set in the spectral data space in such a way that the spectra lie in the region of the spectra to be expected at the respective measuring temperature (also known as a priori correction). In geometric terms, this approach changes the form of calibration spectra as if they had already been recorded at the target temperature. Reference is made here to S. Groß, *Multivariate Korrektur des Temperatureinflusses in der NIR-spektroskopischen Materialfeuchtebestimmung, Dissertation*, Göttingen, 2009 and J. M. Roger et al., EPO-PLS external parameter orthogonalization of PLS application to temperature-independent measurement of sugar content of intact fruits, Chemometrics and intelligent laboratory system, 2003, Vol. 66 (2), pp. 191-204. While the work of Groß relates to the determination of moisture in flour at known temperatures, Rogers et al. are working on what is known as a robust model in which the temperature influences are already taken into account, so that a measurement of the sample temperature is not necessary. In U.S. Pat. No. 10,254,215, proportions of constituent materials of agricultural fruits (such as the sugar content of apples or the oil content of avocado) are measured by the end user by means of a hand-held, compact spectrometer, wherein a temperature measurement of the sample has the purpose of normalizing or modifying the measured spectrum in a manner that is not described in more detail.

Referring now to FIG. 1, schematically a spectrometer arrangement 10 for the acquisition of the content of one or more constituent materials in a sample 12 is shown. A window 14 is arranged within a housing 30, through which a light source 16 subjects the sample 12 lying outside the housing 30 to light. The light can be broadband, or can contain only discrete wavelengths, while the wavelength is usually in the near infrared range. The sample 12 can be stationary with respect to the housing 30, or can move with respect to the housing 30, for example passing it by as a flow of harvested produce in a harvesting machine or as a flow of liquid manure in a manure tank during filling or application, or vice versa, in that the housing 30 is moved along the sample 12 in that it is fastened, for example, to a carriage that is moved over a swath lying on a field.

Light that is reflected from the sample 12 (or, in the event that the light source 16 is arranged outside the housing 30, transmitted through the sample) is analyzed by a spectrometer 18 that is sensitive in the wavelength range of the light source 16 and outputs a spectral signal 20 that indicates the intensity associated with specific wavelengths of the received light. The spectrometer 18 can comprise, in a manner known per se, a dispersive element (e.g. a prism, filter, grating etc.) which deflects the incoming light in directions that depend on the wavelength, said light being received by a plurality of light-sensitive elements (photodiodes, CCDs or the like), each assigned to one wavelength range (see German Patent Appl. DE 199 22 867 C5). In another form of embodiment, only a single light-sensitive element is present, to which the light of different wavelengths is supplied in temporal sequence (cf. European Patent Appl. No. EP 3 444 577 A1). The spectral signal 20 thus contains information regarding the intensities of different wavelengths of the light provided by the light source 16 and reflected from and/or transmitted through the sample 12.

An evaluation device 24, which could also be arranged outside the housing 30, receives the spectral signal 20 as well as a signal 26 that is provided by a sensor 22 that interacts with the sample 12, and when operating calculates an output signal 28 that represents the content of one or more constituent materials in the sample 12 on the basis of the spectral signal 20 and of the signal 26. Calibration data that are stored in a memory 32 are used here. The sensor 22 acquires the temperature and/or the pH value of the sample 12, or any other property such as for example the pressure of the sample, its speed of movement with respect to the housing 30, and/or the air humidity. The sensor 22 could also be arranged at a distance from the housing 30, or replaced or supplemented by an interface with which an operator can enter a suitable value, be it estimated or measured by means of another sensor, or known as a process temperature or the like. The purpose of the signal of the sensor 22 is to compensate for the dependence of the spectra acquired from the sample 12 on the property that is acquired by the sensor 22. This can be done in one of the ways described in more detail below.

FIG. 2 shows a flow diagram according to which the calibration data can be obtained and can be taken into consideration in the evaluation of the spectra. A reference measurement first takes place in step 100 on a sufficiently large number of samples 12, for which purpose one or more spectrometer arrangements 10 can be used, as are shown in FIG. 1. These normally are spectrometer arrangements 10 of the same type as will also be used in the later measurements, but not the same spectrometer arrangements 10. Usually, step 100 is carried out with a plurality of spectrometer arrangements 10 simultaneously or in sequence, in order to be able to compensate for variations in the individual spectrometer arrangements 10. Spectra are thus acquired making use of a number of samples 12 at different, known temperatures, and saved together with the associated temperatures. This means that the spectrum and the associated marginal parameters, e.g. the temperature, are measured at a sample by the spectrometer arrangement 10 simultaneously. An analysis of the samples for specific constituent materials also takes place in a laboratory or at any other desired location on the basis of chemical or physical methods known per se.

Following step 100, the spectra, associated temperatures (measured or made known in some other way, e.g. as a process parameter) and known constituent material contents of the samples are thus available. The calibration data that are stored in the memory 32 are determined in step 102 based on these data.

The measurement with the spectrometer arrangement 10 shown in FIG. 1 then takes place in step 104. On the basis of the temperature (and/or the pH value, or one or more of the other properties referred to above that can be included in the calibration data, instead of or in addition to the temperature, in steps 100 and 102) and the spectral signal 20, the respective constituent material is determined and made available as an output signal 28 for further use, e.g. for documentation purposes or for the control of an actuator.

Specifically, the consideration of the temperature and/or of the pH value and/or of one or more of the other properties can take place in step 104 in such a way that the spectral signal 20 is first subjected to preprocessing and, in the manner usual hitherto, an evaluation, independent of the temperature and/or the pH value, of the constituent material content of the sample takes place on the basis of the calibration data stored in the memory 32. This uncorrected constituent material content can then be corrected based on the temperature and/or another property referred to above, for which purpose a linear or an arbitrary other relationship can be used, for example. Another possibility is that of using different calibration data for different temperatures and/or properties and recalling them from the memory 32 based on the temperature and/or property. It is also possible to modify the spectral signal 20 prior to the evaluation on the basis of the temperature and/or property, and finally to subject it to an evaluation, independent of the temperature and/or the pH value in a manner usual hitherto, of the constituent material content of the sample on the basis of the calibration data stored in the memory 32.

A regression model for the spectrometer 18 with n channels in the form of $i=\Sigma_n x_i c_i + c_0$ based on a calibration dataset with m samples can, for example, be prepared according to the principle of the least squares. i here refers to a constituent material value, e.g. the material moisture, $c_i$ is a set of n regression coefficients, $c_0$, is an offset parameter $x_i$ and are the measured values of the spectrometer that represent the measured spectrum. For this purpose, the measured sensor values are summarized in an n×m matrix $\underline{x}$ (the measured sensor values for each sample are placed in the rows) and the n coefficients $\vec{c}$. A column is in addition included with 1 (written as $\vec{1}$) in order to introduce an offset parameter into the model:

$$[\vec{1}, \underline{x}]_{mx(n+1)} (1, \vec{c})_{n+1} = \vec{i}_m$$

Let $\underline{X} = [\vec{1}, \underline{x}]_{mx(n+1)}$ and $\vec{c} = (1, \vec{c})_{n+1}$ below. The regression coefficients can then be calculated directly with the pseudo-inverses:

$$\vec{c} = (\underline{X}^T \underline{X})^{-1} \underline{X}^T \vec{i}_m$$

This calculation cannot in general be transferred to spectral sensors, since the channels of the spectrometer 18 have high correlations with respect to one another. The principal component or partial least square regression methods are therefore usually applied.

In the principal component regression, the matrix $\underline{x}$ is first subjected to a primary-axis transformation. The eigenvectors of the covariance matrix $K=\text{cov}(\underline{x},\underline{x})$, also known as modes, primary components or loadings, are used as the new basis vectors for the description of the measured sensor values. This means that the matrix is converted into a transformed matrix $\underline{s} = \underline{L}^{-1} \underline{x}^T$, wherein the transformation matrix $L^{-1}$ from the loadings and $\underline{S}$ is the matrix corresponding to $\overline{X}$ in the new coordinate system and is analogous to $\underline{S} = [\vec{1}, \underline{s}]$ above. The coordinates in the transformed coordinate system s are usually known as scores.

A regression model can then be prepared in the new system through:

$$\vec{c}_s = (\underline{S}^T \underline{S})^{-1} \underline{S}^T \vec{i}_m$$

The resulting regression coefficients can be described in the initial system, in that a back-transformation $\vec{c} = \underline{L}\vec{c}_0$ is carried out.

In the calibration process, the regression is only carried out with a few of the n primary components. The complexity of the model can be controlled through the choice of the primary components.

If measured values ($t_i$) of an additional sensor 22 are added to the calibration dataset, and if these are to be taken into consideration in the regression, they can in one variant be grouped to form the sensor values $\underline{X} = [\vec{1}, \vec{t}, \underline{x}]_{mx(n+2)}$ and the model is extended with a coefficient for the temperature measurement value $(1, \vec{c})_{n+1} \rightarrow (1, c_t, \vec{c})_{n+2}$ After this, the primary axis transformation and the subsequent regression to the scores is carried out as before.

Alternatively, the measured values $t_i$ of the sensor 22 are only grouped with the scores after the transformation, i.e. $\underline{S}$ is extended to $[\vec{t}, \underline{S}]$, and the temperature values are treated like one of the primary components and included in the model with a coefficient $c_s'$, i.e. $\vec{c}_s \rightarrow (c_s', \vec{c}_s)$ The back-transformation is then only carried out to the measured values of the spectrometer 18.

Alternatively, separate regression models, as described above, can also be calculated for different temperature ranges and then, with the aid of the temperature sensor, the respective appropriate model for the corresponding material temperature can be selected.

A non-linear model that uses the measured value of the sensor 26 to predict the constituent material can also be used for the prediction. The approach appears particularly promising if a more advanced method of machine (self-)learning, such as for example a neural network 34, wherein the spectral measurements of the spectrometer 18 and the measured values of the sensor 26 are used as input values, is used for the prediction. This means that the measured values of the sensor 26 are taken as the input into, for example, a neural network 34 (FIG. 3). The network 34 is then trained with the measured values of the spectrometer 18 and those of the independent (temperature) sensor 22, and then the measured values of the sensor 22 and of the spectrometer 18 are used in operation. In this example, a control model comprising an artificial neural network is utilized. The artificial neural network comprises a plurality of neural nodes including a set of input nodes for receiving an input (spectrometer 18 and values of sensor 26) to the artificial neural network and a set of output nodes for outputting an output (target value 28) to the artificial neural network, where each neural node represents a sub-function for determining an output for the artificial neural network from the input of the artificial neural network, and each input node is connected to one or more output nodes by a connection of a plurality of weighted connections; and a function configured to generate actions for the agricultural work machine 40 which improve its operation, the function defined by the sub-functions and weighted connections of the artificial neural network.

The artificial neural network may be a first artificial neural network from a pair of similarly configured artificial neural networks acting as an actor-critic pair and used to train the first artificial neural network to generate actions that improve the agricultural work machine 40 performance. The first neural network inputs state vectors and values for the weighted connections and outputs action vectors, the values for the weighted connections modifying the function for generating actions for the agricultural work machine 40 that improve its performance, and the second neural network inputting a reward vector and a state vector and outputting the values for the weighted connections, the reward vector comprising elements signifying the improvement in performance of the agricultural work machine from a previously executed action.

An agricultural work machine 40 in the form of a manure tank that is pulled across a field by an agricultural tractor 42 in order to apply liquid manure onto a field through a line 44 is illustrated in FIG. 4. The output signal 28 of the spectrometer arrangement 10, which interacts with the liquid manure flowing in the line 44, is supplied to a controller 48 that is additionally connected to a position determination system 46. The controller 48 controls a valve 50 that determines the rate at which the liquid manure flows through the line 44, on the basis of an application map previously stored in the controller 48 in which it is specified how much constituent material (e.g. nitrogen, potassium etc.) is to be applied per unit area, and on the basis of the output signal 28, for the purpose of maintaining the values specified in the application map. In this form of embodiment, the sensor 22 of the spectrometer arrangement 10 acquires in particular the temperature of the sample 12 and, optionally, also its pressure and/or pH value. Its output values are used to correct the output signal 28 in one of the ways described above.

Figure 5:
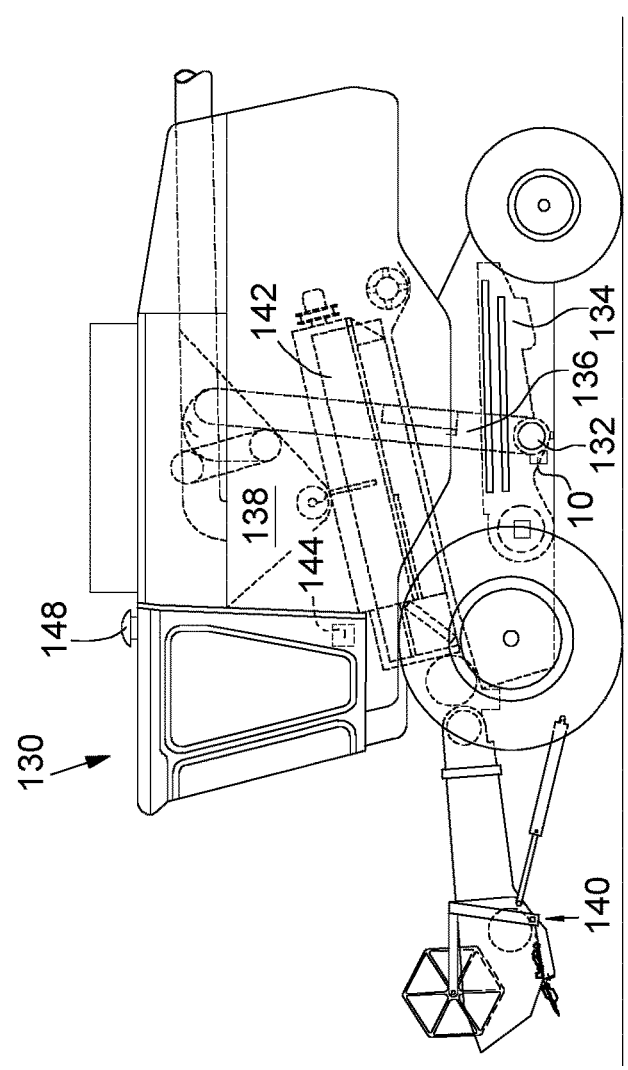
FIG. 5 shows a side view of an agricultural work machine in the form of a combine harvester with a spectrometer arrangement.

FIG. 5 shows a further form of embodiment of a work machine 130 in the form of a self-driving combine harvester 130 that is fitted with a spectrometer arrangement 10. The spectrometer arrangement 10 is attached to the wall of a cross-feeding auger 132, and interacts through an opening in the wall with the cleaned harvested product (grains) that is output from a cleaning device 134, and transferred by the cross-feeding auger 132 to a grain elevator 136 that places it in a grain tank 138. The cleaning device 134 obtains the harvested product from a harvested product receiving device 140 that supplies it to a threshing and separating unit 142. The spectrometer arrangement 10 supplies particular information relating to the constituent material such as protein content, starch content, oil content and the proportion of moisture in the harvested grain; this is stored by a control unit 144 in a map together with position information that is provided by a receiving antenna 148 of a satellite-based position determination system. The sensor 22 in this form of embodiment acquires the temperature of the sample 12 and optionally also the air humidity in the surroundings of the work machine 130 and/or the flow rate of the grains being sensed. Its output values are used to correct the output signal 28, in particular from the point of view of the moisture content of the harvested product, in one of the ways described above.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency trade-offs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the systems, methods, processes, apparatuses and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The foregoing detailed description has set forth various embodiments of the systems, apparatuses, devices, methods and/or processes via the use of block diagrams, schematics, flowcharts, examples and/or functional language. Insofar as such block diagrams, schematics, flowcharts, examples and/or functional language contain one or more functions and/or operations, it will be understood by those within the art that each function and/or operation within such block diagrams, schematics, flowcharts, examples or functional language can be implemented, individually and/or collectively, by a wide range of hardware, software, firmware, or virtually any combination thereof. In one example, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the signal bearing medium used to carry out the distribution. Examples of a signal bearing medium include, but are not limited to, the following: a computer readable memory medium such as a magnetic medium like a floppy disk, a hard disk drive, and magnetic tape; an optical medium like a Compact Disc (CD), a Digital Video Disk (DVD), and a Blu-ray Disc; computer memory like random access memory (RAM), flash memory, and read only memory (ROM); and a transmission type medium such as a digital and/or an analog communication medium like a fiber optic cable, a waveguide, a wired communications link, and a wireless communication link.

The herein described subject matter sometimes illustrates different components associated with, comprised of, contained within or connected with different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two or more components herein combined to achieve a particular functionality can be seen as "associated with" each other such that the desired functionality is achieved, irrespective of architectures or intermediate components. Likewise, any two or more components so associated can also be viewed as being "operably connected", or "operably coupled", to each other to achieve the desired functionality, and any two or more components capable of being so associated can also be viewed as being "operably couplable", to each other to achieve the desired functionality. Specific examples of operably couplable include, but are not limited to, physically mateable and/or physically interacting components, and/or wirelessly interactable and/or wirelessly interacting components, and/or logically interacting and/or logically interactable components.

Unless specifically stated otherwise or as apparent from the description herein, it is appreciated that throughout the present disclosure, discussions utilizing terms such as "accessing," "aggregating," "analyzing," "applying," "brokering," "calibrating," "checking," "combining," "communicating," "comparing," "conveying," "converting," "correlating," "creating," "defining," "deriving," "detecting," "disabling," "determining," "enabling," "estimating," "filtering," "finding," "generating," "identifying," "incorporating," "initiating," "locating," "modifying," "obtaining," "outputting," "predicting," "receiving," "reporting," "retrieving," "sending," "sensing," "storing," "transforming," "updating," "using," "validating," or the like, or other conjugation forms of these terms and like terms, refer to the actions and processes of a control unit, computer system or computing element (or portion thereof) such as, but not limited to, one or more or some combination of: a visual organizer system, a request generator, an Internet coupled computing device, a computer server, etc. In one example, the control unit, computer system and/or the computing element may manipulate and transform information and/or data represented as physical (electronic) quantities within the control unit, computer system's and/or computing element's processor(s), register(s), and/or memory(ies) into other data similarly represented as physical quantities within the control unit, computer system's and/or computing element's memory(ies), register(s) and/or other such information storage, processing, transmission, and/or display components of the computer system(s), computing element (s) and/or other electronic computing device(s). Under the direction of computer-readable instructions, the control unit, computer system(s) and/or computing element(s) may carry out operations of one or more of the processes, methods and/or functionalities of the present disclosure.

Those skilled in the art will recognize that it is common within the art to implement apparatuses and/or devices and/or processes and/or systems in the fashion(s) set forth herein, and thereafter use engineering and/or business practices to integrate such implemented apparatuses and/or devices and/or processes and/or systems into more comprehensive apparatuses and/or devices and/or processes and/or systems. That is, at least a portion of the apparatuses and/or devices and/or processes and/or systems described herein can be integrated into comprehensive apparatuses and/or devices and/or processes and/or systems via a reasonable amount of experimentation.

Although the present disclosure has been described in terms of specific embodiments and applications, persons skilled in the art can, considering this teaching, generate additional embodiments without exceeding the scope or departing from the spirit of the present disclosure described herein. Accordingly, it is to be understood that the drawings and description in this disclosure are proffered to facilitate comprehension of the present disclosure and should not be construed to limit the scope thereof.

As used herein, unless otherwise limited or modified, lists with elements that are separated by conjunctive terms (e.g., "and") and that are also preceded by the phrase "one or more of" or "at least one of" indicate configurations or arrangements that potentially include individual elements of the list, or any combination thereof. For example, "at least one of A, B, and C" or "one or more of A, B, and C" indicates the possibilities of only A, only B, only C, or any combination of two or more of A, B, and C (e.g., A and B; B and C; A and C; or A, B, and C).

What is claimed:

1. A material evaluating apparatus for an agricultural work machine comprising:
   interface circuitry;
   computer-readable instructions; and
   at least one processor circuit to be programmed by the computer-readable instructions to:
   cause a light source to illuminate a sample of a material in a tank of the agricultural work machine;
   determine a spectral signal related to a wavelength-specific intensity of light reflected by a constituent material of the sample;
   determine a prediction of a content of the constituent material using a neural network, the neural network to use the spectral signal of a spectrometer, calibration data, and a property signal relating to a property of the sample, the property signal to include at least one of a temperature, a pH, a flow rate, an air humidity, and/or a pressure of the sample; and cause an actuator of the agricultural work machine to change an application rate of the material in the tank based on the prediction of the content of the constituent material.

2. The material evaluating apparatus of claim 1, wherein the constituent material is representative of the content of the material associated with the tank of the agricultural work machine.

3. The material evaluating apparatus of claim 2, wherein one or more of the at least one processor circuit is to generate the property signal, the generation of the property signal by at least one of a sensor that interacts with the sample or a user input inputted via a user interface.

4. The material evaluating apparatus of claim 3, wherein one or more of the at least one processor circuit is to:
determine the prediction of the content of the constituent material using at least in part the calibration data; and
correct the determined prediction of the content using at least in part the property signal.

5. The material evaluating apparatus of claim 3, wherein the actuator of the agricultural work machine is activated at a location of a geo-referenced map corresponding to the content of the constituent material.

6. The material evaluating apparatus of claim 2, wherein one or more of the at least one processor circuit is to determine the spectral signal using at least in part the property signal.

7. The material evaluating apparatus of claim 2, wherein one or more of the at least one processor circuit is to determine the calibration data using at least the property signal.

8. The material evaluating apparatus of claim 2, wherein the content of the constituent material in the sample is stored as a location in a geo-referenced map.

9. The material evaluating apparatus of claim 1, wherein one or more of the at least one processor circuit is to generate the calibration data using the neural network.

10. The material evaluating apparatus of claim 9, wherein the neural network is trained using the spectral signal.

11. The material evaluating apparatus of claim 10, including:
neural nodes including a set of input nodes for receiving an input to the neural network and a set of output nodes for outputting an output to the neural network, where the neural nodes represent a sub-function for determining the output for the neural network from the input of the neural network, and the input nodes are connected to the output nodes by weighted connections; and
a function to generate actions for the agricultural work machine which improve a performance of the agricultural work machine, the function defined by the sub-functions and weighted connections of the neural network.

12. The material evaluating apparatus of claim 11, wherein the neural network is a first neural network from a pair of similarly configured neural networks acting as an actor-critic pair and used to train the first neural network to generate the actions that improve the performance of the agricultural work machine.

13. The material evaluating apparatus of claim 12, wherein the first neural network inputs state vectors and values for the weighted connections and outputs action vectors, the values for the weighted connections modifying the function for generating the actions for the performance of the agricultural work machine that improve the performance of the agricultural work machine, and a second neural network inputs a reward vector and a state vector and outputs the values for the weighted connections, the reward vector including elements signifying the improvement in the performance of the agricultural work machine from a previously executed action.

14. The material evaluating apparatus of claim 1, wherein the agricultural work machine includes a manure tank one or more of the at least one processor circuit is to evaluate the constituent material of the manure tank and, using the content of the constituent material, control operation of the manure tank.

15. The material evaluating apparatus of claim 14, wherein the apparatus interacts with liquid manure within the manure tank and the liquid manure flowing in and out of the manure tank.

16. The material evaluating apparatus of claim 1, wherein one or more of the at least one processor circuit is to change the application rate of the constituent material based on an application map, the application map to specify an amount of a component of the constituent material per unit area.

17. At least one non-transitory computer-readable medium comprising computer-readable instructions to cause at least one processor circuit to at least:
cause a light source to illuminate a sample of material in a tank of an agricultural work machine;
determine a spectral signal related to a wavelength-specific intensity of light reflected by a constituent material of the sample;
determine a prediction of a content of the constituent material using a neural network, the neural network to use the spectral signal of a spectrometer, calibration data, and a property signal relating to a property of the sample, the property signal to include at least one of a temperature, a pH, a flow rate, an air humidity, and/or a pressure of the sample; and
cause an actuator of the agricultural work machine to change an application rate of the material in the tank based on the prediction of the content of the constituent material.

18. The at least one non-transitory computer-readable medium of claim 17, wherein the computer-readable instructions are to cause one or more of the at least one processor circuit to generate the calibration data using the neural network.

19. A method to evaluate a material, the method including:
causing a light source to illuminate a sample of the material in a tank of an agricultural work machine;
determining, by at least one processor circuit programmed by at least one instruction, a spectral signal related to a wavelength-specific intensity of light reflected by a constituent material of the sample;
determining, by one or more of the at least one processor circuit, a prediction of a content of the constituent material using a neural network, the neural network using the spectral signal of a spectrometer, calibration data, and a property signal relating to a property of the sample, the property signal to include at least one of a temperature, a pH, a flow rate, an air humidity, and/or a pressure of the sample; and
causing, by one or more of the at least one processor circuit, an actuator of the agricultural work machine to change an application rate of the material in the tank based on the prediction of the content of the constituent material.

20. The method of claim 19, further including generating the calibration data using the neural network.

\* \* \* \* \*

UNITED STATES PATENT AND TRADEMARK OFFICE
CERTIFICATE OF CORRECTION

| | |
|---|---|
| PATENT NO. | : 12,228,504 B2 |
| APPLICATION NO. | : 17/248895 |
| DATED | : February 18, 2025 |
| INVENTOR(S) | : Schade et al. |

It is certified that error appears in the above-identified patent and that said Letters Patent is hereby corrected as shown below:

In the Claims

In Column 12, Claim 14, Line 6, Delete "manure tank one or" and insert --manure tank and one or--.

Signed and Sealed this
Thirtieth Day of September, 2025

John A. Squires
*Director of the United States Patent and Trademark Office*